United States Patent
Chou et al.

(10) Patent No.: US 9,279,782 B2
(45) Date of Patent: Mar. 8, 2016

(54) GAS SENSOR

(71) Applicant: National Taiwan University of Science and Technology, Taipei (TW)

(72) Inventors: Chen-Chia Chou, Taipei (TW); Tsung-Her Yeh, Taipei (TW); Wei-Wei Duan, Taipei (TW); Jyh-Shiarn Cherng, Taipei (TW); Ruei-De Lin, Taipei (TW)

(73) Assignee: NATIONAL TAIWAN UNIVERSITY OF SCIENCE AND TECHNOLOGY, Taipei (TW)

( * ) Notice: Subject to any disclaimer, the term of this patent is extended or adjusted under 35 U.S.C. 154(b) by 450 days.

(21) Appl. No.: 13/855,805

(22) Filed: Apr. 3, 2013

(65) Prior Publication Data
US 2014/0083851 A1 Mar. 27, 2014

(30) Foreign Application Priority Data
Sep. 21, 2012 (TW) .............................. 101134669 A

(51) Int. Cl.
*G01N 27/407* (2006.01)
(52) U.S. Cl.
CPC .......... *G01N 27/407* (2013.01); *G01N 27/4071* (2013.01); *G01N 27/4075* (2013.01)
(58) Field of Classification Search
CPC .......................... G01N 27/4071; G01N 27/409
See application file for complete search history.

(56) References Cited

U.S. PATENT DOCUMENTS 4,040,929 A * 8/1977 Bauer et al. ................... 204/426

OTHER PUBLICATIONS 3 pages (cover page, bibliographic data page, and p. 206).from The CRC Handbook of Solid State Electrochemistry, ed. P.J. Gellings and H.J.M. Bouwmeester, 1997 by CRC Press, Inc.*

* cited by examiner

*Primary Examiner* — Alexander Noguerola
(74) *Attorney, Agent, or Firm* — Bacon & Thomas, PLLC

(57) ABSTRACT

A gas sensor comprises a layered structure with an ionic conductive film and a high gas-permeability interlayer film, a first catalyst electrode and a second catalyst electrode, a conductivity promotion structure, a high-k layer and a current detecting unit. The ionic conductive film includes a material with ionic conductivity ranging from 0.02 to 1000 S/cm. The first catalyst electrode and second catalyst electrode are located on the layered structure and spaced by a predetermined distance for ionizing a gas and reducing the ionized gas, respectively. The conductivity promotion structure includes a material with electronic conductivity ranging from $10^{-5}$ to $10^5$ S/cm, and provides wanted electrons for a reduction reaction. The high-k layer is interposed between the conductivity promotion structure and layered structure. The current detecting unit is coupled to the first catalyst electrode and second catalyst electrode to sense a detecting current with respect to the ionized gas.

11 Claims, 11 Drawing Sheets

GAS SENSOR

BACKGROUND OF THE INVENTION (1) Field of the Invention

The present invention relates to a gas sensor, particularly for a current-type gas sensor.

(2) Description of the Prior Art

Basically, current popular conventional gas sensors according to the operation mechanism can be categorized into following types: catalytic combustion type, oxide semiconductor type, solid state electrolyte type (using sensing electric voltage, current or resistance as signal), field-effect transistor type (FET), infrared type and so on. By electrode configuration of the conventional technology, the popular conventional gas sensors can further be classified into electrode coplanar configuration and electrode un-coplanar configuration. In the early phases, the conventional gas sensors of electrode un-coplanar configuration take the dominance, which are further sorted into tubular profile, planar profile and compound profile. Whereas, the conventional gas sensors of electrode coplanar configuration are apt to be adopted in popular manner because the thin-film technology is gradually improved and advanced. Moreover, the gas sensors can be grouped into electric voltage signal kind and electric current signal kind in accordance with the sensing method and detecting signal. Nowadays, a combinational gas sensor in merging the electric voltage signal kind and electric current signal kind emerges from the automobile industry.

FIG. 1 is an illustrative schematic view for a conventional current-type oxygen sensor 10. As shown in the figure, the oxygen sensor 10 comprises a first catalyst electrode 11, a second catalyst electrode 12, an electrolyte layer 13, a gas diffusion cavity 14 with a gas diffusion opening 17, a power supply 15 and a galvanometer or current meter 16. The power supply 15, which is usually a battery, is electrically connected to both of the first catalyst electrode 11 and the second catalyst electrode 12. The current meter 16 is parallel connected to the power supply 15. The first catalyst electrode 11 is located in the gas diffusion cavity 14. The gas diffusion opening 17 is bored at the top surface of the gas diffusion cavity 14.

Upon performing detecting operation, the power supply 15 will provide a voltage to both of the first catalyst electrode 11 and second catalyst electrode 12 to initiate of the gas sensor 10 so the oxygen gas is enabled to enter into the gas diffusion cavity 14 via the gas diffusion opening 17. In the gas diffusion cavity 14, the oxygen gas is chemically is ionized into oxygen ion by the first catalyst electrode 11 so a limiting current is generated by the flow of gas ions and/or electrons from the first catalyst electrode 11 to the second catalyst electrode 12 by the oxygen vacancies in the electrolyte layer 13. Thereby, by measuring the magnitude of the limiting current via the current meter 16, the ambient oxygen concentration can be determined. Normally, the measured limiting current signal value of the current meter 16 is direct proportional to the partial oxygen pressure in the ambient atmosphere.

Regarding the conventional current-type gas sensor, the thickness of the electrolyte layer 13 will affect the sensitivity of the gas sensor 10, which means the thinner for the thickness of the electrolyte layer 13, the better for the sensitivity of the gas sensor 10 is. However, subjecting to the material feature of the electrolyte layer 13, the thickness reducing of the electrolyte layer 13 has its critical limit otherwise it is susceptible to break if it exceeds its critical limit. Moreover, the conventional current-type gas sensor requires operating in higher working temperature for keeping stability because the conductor material of able ionization adopted by the conventional electrolyte layer 13 is almost solid electrolyte. Accordingly, an extra conventional heating accessory is needed to maintain the higher working temperature. However, if sudden fluctuation happens in the ambient temperature, the conventional heating accessory is usually unable to adequately response in adjustment for the suitably corresponding working temperature with result that the detecting accuracy of the conventional current-type gas sensor is harmfully affected.

SUMMARY OF THE INVENTION

Having realized foregoing issue and demand, the inventor of the present invention elaborately performs long term research and development on the basis of personal experience accumulated from practical application of many years. Eventually, a brand-new gas sensor of the present invention is worked out. The primary object of the present invention is to provide a gas sensor with features of high stability, comprehensive applicability and capability for solving existing drawbacks in the conventional gas sensor.

The present invention provides a current-type gas sensor comprising a layered structure, a first catalyst electrode, a second catalyst electrode, a conductivity promotion structure, a high-k layer (k denotes dielectric constant) and a current detecting unit. The layered structure includes an ionic conductive film and a high gas-permeability interlayer film stacked in an alternative manner. The thickness of the ionic conductive film is greater than or equivalent to that of the high gas-permeability interlayer film. The ionic conductive film is made of ionic material with thickness in range of 1 to 500 nanometers, and ionic conductivity in range of 0.02 to 1,000 S/cm. The first catalyst electrode and the second catalyst electrode are disposed on the layered structure or at a lateral side of the layered structure with a gap or an interspace therebetween. A gas is ionized at the first catalyst electrode into gaseous ions, and the gaseous ions move to the second catalyst electrode via the high gas-permeability interlayer film of the layered structure such that the gaseous ions can be reduced by an reduction reaction at the second catalyst electrode. A voltage required to generate a detecting current is also provided by the first catalyst electrode and the second catalyst electrode. The conductivity promotion structure is made of a material with electronic conductivity in range of $10^{-5}$ to $10^5$ S/cm for serving as a electron sink to is provide free electrons to enhance foregoing dissociating and reduction reactions. The high-k layer is sandwiched between the layered structure and the conductivity promotion structure, wherein the k denotes dielectric constant. The current detecting unit is electrically connected to the first catalyst electrode and the second catalyst electrode to detect and measure detecting current.

In an exemplary embodiment, the ionic conductive film for the current-type gas sensor in the present invention is made of ionic material with thickness in range of 1 to 500 nanometers, and the thickness of the ionic conductive film is greater than or equivalent to that of the high gas-permeability interlayer film.

In another exemplary embodiment, the current-type gas sensor in the present invention further comprises an active thermal control module including a heating unit and a temperature control unit, and the heating unit is used to heat the layered structure while the temperature control unit is used to monitor and control the heating unit for the purpose of controlling the power output of the heating unit.

In the other exemplary embodiment, the current detecting unit can be replaced by a voltage detecting unit to form a voltage-type gas sensor.

The other objects and features of the present invention can be further understood from the disclosure in the specification.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. In this regard, directional terminology, such as "top," "bottom," "front," "back," etc., is used with reference to the orientation of the Figure(s) being described. The components of the present invention can be positioned in a number of different orientations. As such, the directional terminology is used for purposes of illustration and is in no way limiting. On the other hand, the drawings are only schematic and the sizes of components may be exaggerated for clarity. It is to be understood that other embodiments may be utilized and structural changes may be made without departing from the scope of the present invention. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. Similarly, the terms "facing," "faces" and variations thereof herein are used broadly and encompass direct and indirect facing, and "adjacent to" and variations thereof herein are used broadly and encompass directly and indirectly "adjacent to". Therefore, the description of "A" component facing "B" component herein may contain the situations that "A" component facing "B" component directly or one or more additional components is between "A" component and "B" component. Also, the description of "A" component "adjacent to" "B" component herein may contain the situations that "A" component is directly "adjacent to" "B" component or one or more additional components is between "A" component and "B" component. Accordingly, the drawings and descriptions will be regarded as illustrative in nature and not as restrictive.

Figure 1:
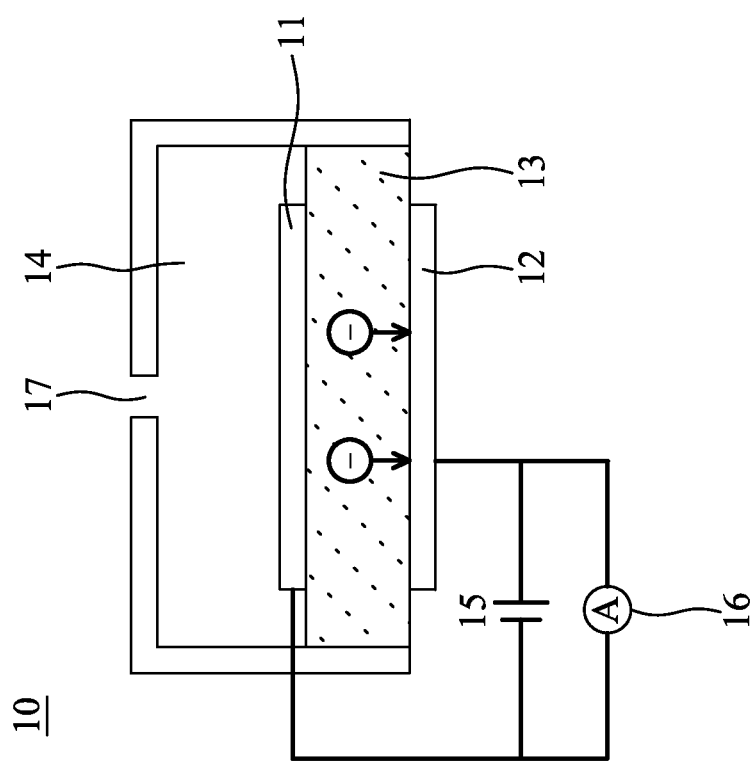
FIG. 1 is an illustrative schematic view for a conventional current-type oxygen sensor.
Figure 2:
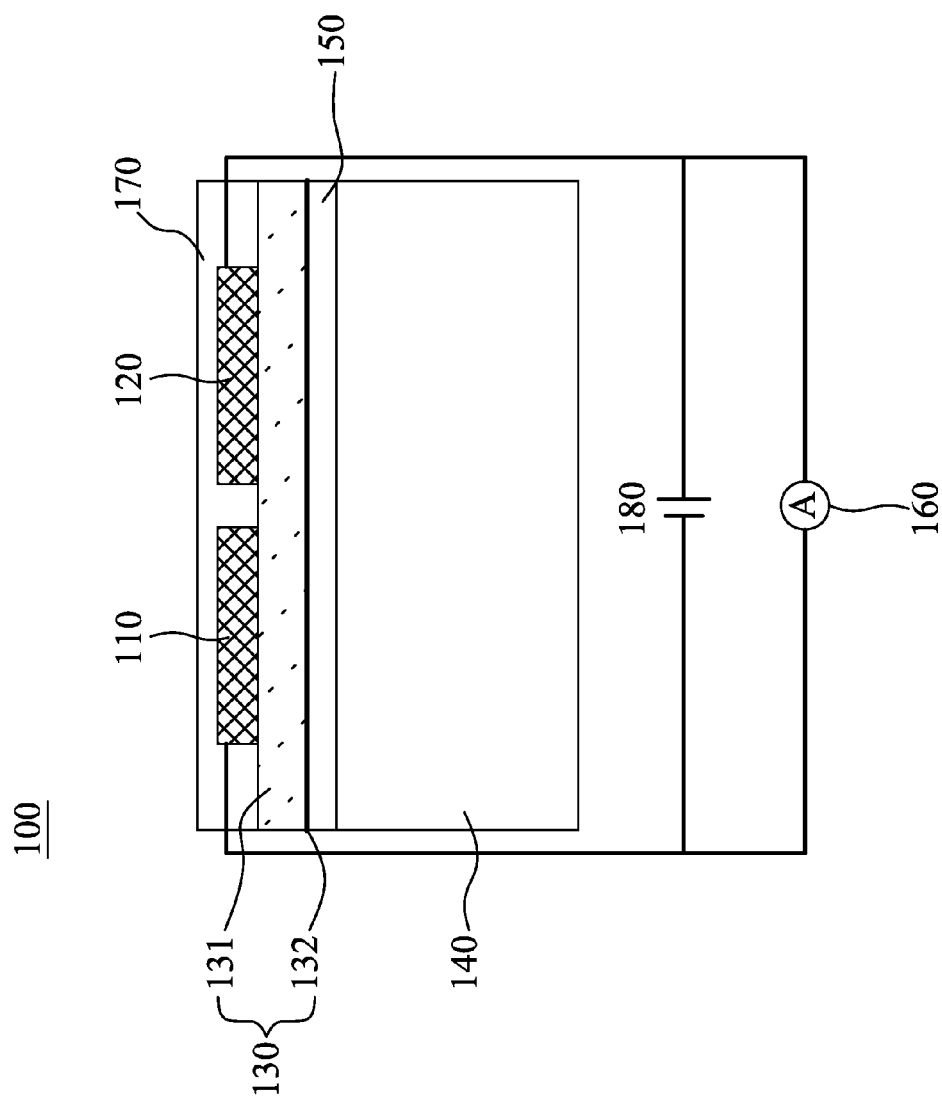
FIG. 2 is an illustrative schematic view for a current-type gas sensor in the first preferred exemplary embodiment of the present invention.

FIG. 2 is an illustrative schematic view for a current-type gas sensor 100 in the first preferred exemplary embodiment of the present invention.

As shown in the FIG. 2, the gas sensor 100 comprises a layered structure 130, a first catalyst electrode 110, a second catalyst electrode 120, a gas diffusion layer 170, a power supply 180, a conductivity promotion structure 140, a high-k layer (k denotes dielectric constant) 150 and a current detecting unit 160.

The layered structure 130, which is preferably disposed on the high-k layer 150, includes an ionic conductive film 131 and a high gas-permeability interlayer film 132 stacked in an alternative manner. The size of the ionic conductive film 131 is bigger than that of the high gas-permeability interlayer film 132. The ionic conductive film 131 is made of ionic material with thickness in range of 1 to 500 nanometers, and ionic conductivity in range of 0.02 to 1,000 S/cm.

Figure 3:
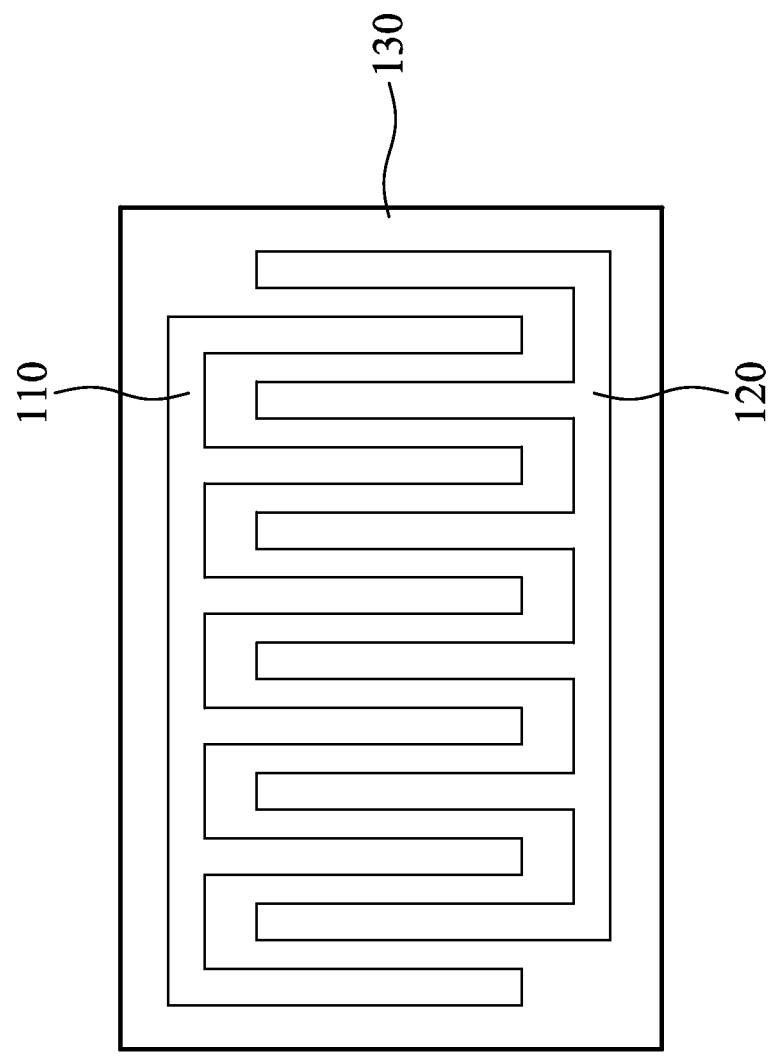
FIG. 3 is an illustrative schematic view showing a typical configuration of the first catalyst electrode and second catalyst electrode for a current-type gas sensor in the first preferred exemplary embodiment of the present invention.

The first catalyst electrode 110 and the second catalyst electrode 120, which are disposed on an upper surface of the layered structure 130, are preferably interdigitated with mutually interspaced (as shown in FIG. 3) to increase the sensing area thereof and shorten the mutual interspace or the gap therebetween.

The gas diffusion layer 170 fully covers the first catalyst electrode 110 and second catalyst electrode 120 as well as the layered structure 130.

The power supply 180, which is electrically connected to the first catalyst electrode 110 and the second catalyst electrode 120 preferably, provides potential energy to the first catalyst electrode 110 and the second catalyst electrode 120 so the natural gas to be sensed at the first catalyst electrode 110 is ionized into gaseous ions status while the ionized gaseous ions at the second catalyst electrode 120 are reduced back to non-ionic natural gas status.

The conductivity promotion structure 140 is made of a material with electronic conductivity in range of $10^{-5}$ to $10^5$ S/cm to provide free electrons to enhance foregoing dissociating and reduction reactions.

The high-k layer 150 is sandwiched between the layered structure 130 and the conductivity promotion structure 140 to isolate both of which.

The current detecting unit 160 such as galvanometer or current meter, which is electrically connected to the first catalyst electrode 110 and the second catalyst electrode 120 in parallel with the power supply 180, to preferably detect and measure an electric current interflowing between the first catalyst electrode 110 and the second catalyst electrode 120. In an embodiment, the electric current is a limiting current.

Figure 2A:
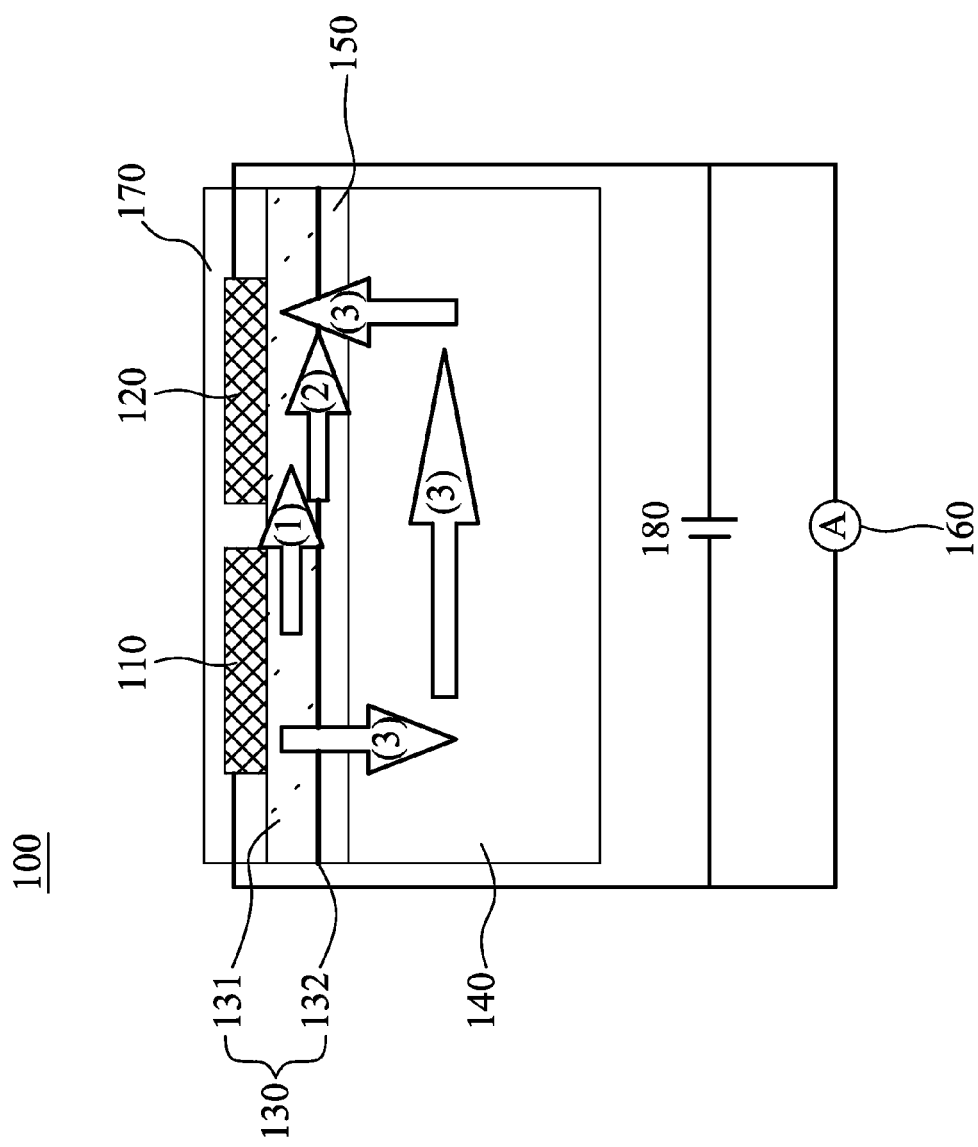
FIG. 2A is an illustrative schematic view showing three paths for generated detecting electric current by the current-type gas sensor in the first preferred exemplary embodiment of the present invention.

FIG. 2A takes oxygen gas as example to show three paths for generated a detecting electric current by the current-type gas sensor in the first preferred exemplary embodiment of the present invention. When the power supply 180 provides potential energy to the first catalyst electrode 110 and the second catalyst electrode 120, the natural oxygen gas molecule ($O_2$) to be sensed at the first catalyst electrode 110 is ionized into gaseous oxygen ions ($O^{2-}$) status while the ionized gaseous oxygen ions ($O^{2-}$) at the second catalyst electrode 120 are reduced back to non-ionic natural oxygen gas molecule ($O_2$) status.

In path (1), partial oxygen ions ($O^{2-}$) ionized at the first catalyst electrode 110 are permeated into the ionic conductive film 131 and moved to the second catalyst electrode 120, where the ionized gaseous oxygen ions ($O^{2-}$) are reduced back to non-ionic natural oxygen gas molecule ($O_2$) status for releasing out. Normally, a higher working temperature in operating the gas sensor 100 is required for the path (1) because it purely relies on the ionic conductive film 131 due to completely being proceeded therein.

In path (2), the high gas-permeability interlayer film 132 serves as another path for generated a detecting electric current as the high gas-permeability interlayer film 132 is full of oxygen vacancies. By these oxygen vacancies, a lot of oxygen ions ($O^2$) are moved from the first catalyst electrode 110 to the second catalyst electrode 120 for reducing back to non-ionic natural oxygen gas molecule ($O_2$) status upon potential difference applied between the first catalyst electrode 110 and the second catalyst electrode 120 by the power supply 180.

Figure 2B:
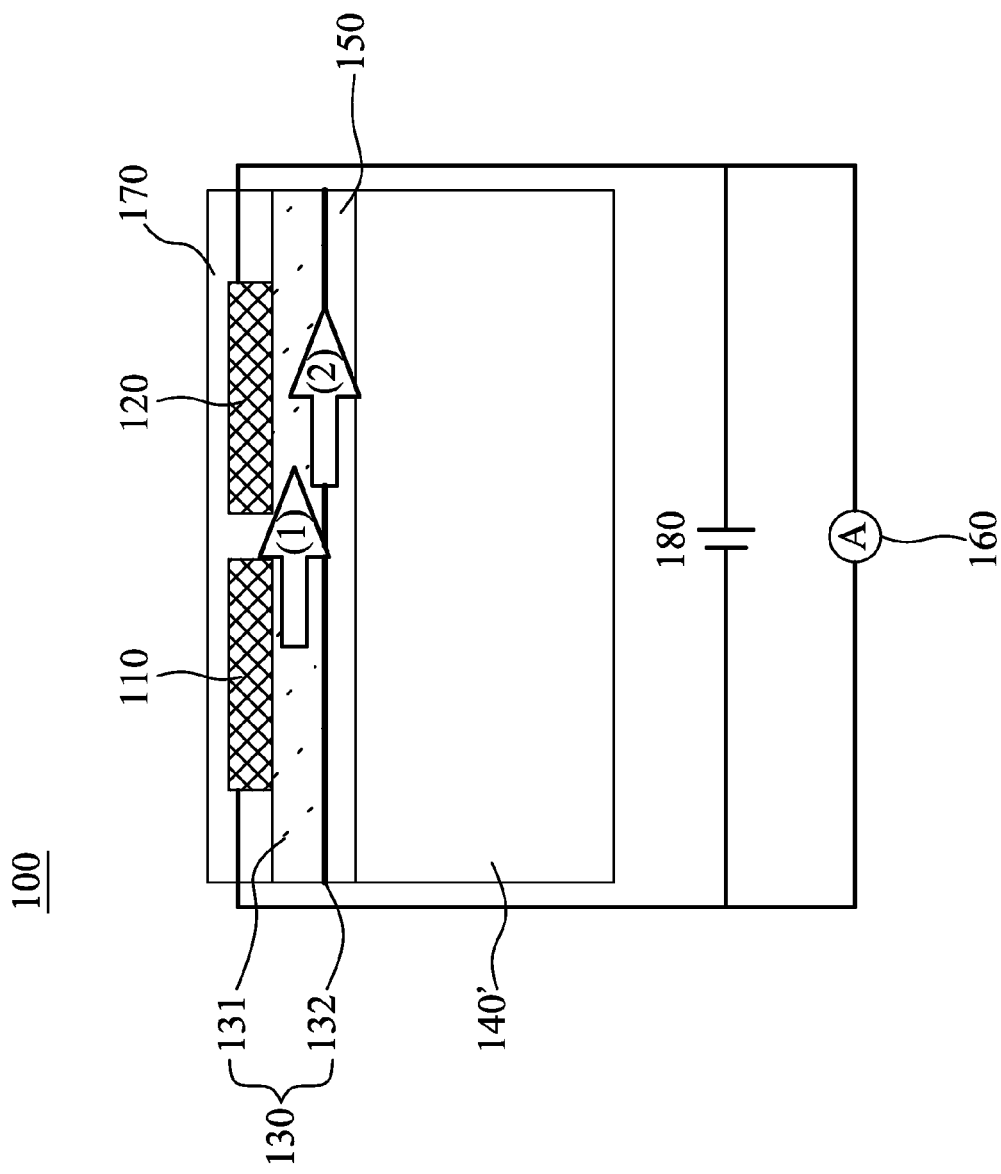
FIG. 2B is an illustrative schematic view showing the generated electric current by the current-type gas sensor under lack of conductivity promotion structure in the first preferred exemplary embodiment of the present invention.

In path (3), because all thicknesses of the ionic conductive film 131 and the high gas-permeability interlayer film 132 are in nanometer scale, a lot of free electrons generated in the conductivity promotion structure 140 are penetrated through the layered structure 130 to the first catalyst electrode 110 by the tunneling effect, and vice versa. The conductivity promotion structure 140 serves as a electron sink for provide more free electrons interflowing between the first catalyst electrode 110 and second catalyst electrode 120, so more oxygen ions ($O^{2-}$) are created. With these interflowing free electrons by the tunneling effect, the gas sensor 100 in the present invention can even operate under low temperature as in room temperature. Contrastively, please refer to a non-conductivity promotion structure 140' of the gas sensor 100' shown in the FIG. 2B, which lacks of the conductivity promotion structure 140 shown in the FIG. 2 or FIG. 2A. Without free electrons generated by the conductivity promotion structure 140, all the detecting electric currents solely rely on the oxygen ions ($O^{2-}$) created in path (1) and path (2), a higher working temperature in operating the gas sensor 100' is required even the existing of the high gas-permeability interlayer film 132.

The reaction rate of abovementioned reaction increases when the concentration of oxygen contained in the ambient atmosphere. Therefore, more carriers flow from the first catalyst electrode 110 to the second catalyst electrode 120, and the larger limiting current is measured by the current detecting unit. The partial concentration of the reacting oxygen contained in the ambient atmosphere can be effectively detected by the gas sensor 100 of the present invention.

In addition, the measuring sensibility of the gas sensor 100 in the present invention is adjusted by adjusting the transverse displacement of the reacting gaseous ion and/or electron. For the gas sensor 100 of the present invention, the transverse displacement is normally the distance between the first catalyst electrode 110 and the second catalyst electrode 120, and the transverse displacement is controllable by the ordinary semiconductor process. Therefore, the gas sensor 100 of the present invention has potential in suitably application in the sensing environment, which requires high sensibility.

Regarding the gas sensor 100 in the present invention, the material of the first catalyst electrode 110 and the second catalyst electrode 120 can select from metals such as platinum, gold, palladium, rhodium, Iridium, ruthenium, osmium, nickel, cobalt, aluminum and iron etc., each of which is easy to form electrochemical reaction with gaseous oxygen, or the perovskite family of ceramic materials such as $LaSrMnO_3$ or $LaSrCoFeO_3$, each of which is easy to form electrochemical reaction with gaseous oxygen, or the composites formed by zirconia with foregoing metals or ceramic materials to provide conductivity for both of free ions and electrons. Moreover, for the composing materials in the first catalyst electrode 110 and the second catalyst electrode 120, an extra second material of property-modifying additive such as copper, cerium oxide etc. can be added to enhance anti-carbon, antitoxic and anti-sulfuring capabilities. The material of the gas diffusion layer 170 can select from serial materials of aluminum spinel, magnesium spinel, lanthanum aluminate, or the composites formed with foregoing aluminum spinel, magnesium spinel and lanthanum aluminate. Similarly, for the composing materials of the gas diffusion layer 170, an extra second material of property-modifying additive such as copper, cerium oxide etc. can also be added to enhance anti-carbon, antitoxic and anti-sulfuring capabilities. The material of the high-k layer 150 can select from serial materials of silicon oxide ($SiO_x$), zirconia and cerium oxide etc. each of which has high dielectric constant (k) and fixed oxygen content.

Besides, certain operating statuses such as working temperature, externally applied voltage and feedback current signal etc. will be affected by the parameters such as thickness of the ionic conductive film 131, the thickness of the high gas-permeability interlayer film 132 and the match with the conductivity promotion structure 140. Moreover, the thickness of the high-k layer 150 is also an important parameter for affecting behavior of electron in tunneling effect. For the exemplary preferred embodiment of the present invention, the thickness range of the ionic conductive film 131 is in scale of 1 to 500 nanometers, the thickness range of the high gas-permeability interlayer film 132 is in scale of 1 to 50 nanometers while the thickness range of the high-k layer 150 is in scale of 1 to 500 nanometers. All the foregoing film layers of the ionic conductive film 131, the high gas-permeability interlayer film 132 and the high-k layer 150 can be fabricated by the micro electro-mechanical systems (MEMS) such as screen printing process, electroplating process, sputtering process or evaporation process etc.

FIG. 3 shows a typical configuration of the first catalyst electrode 110 and the second catalyst electrode 120 for a current-type gas sensor in the first preferred exemplary embodiment of the present invention. In the preferred exemplary embodiment of the present invention, the first catalyst electrode 110 and the second catalyst electrode 120 are in mutual coplanar interdigitated configuration to minimize the interspace or gap and to maximize the sensing area of the first catalyst electrode 110 and the second catalyst electrode 120 so the sensibility of the gas sensor 100 can be enhanced due to increasing of the detecting electric current. Foregoing first catalyst electrode 110 and second catalyst electrode 120 can be fabricated by any kind of thick film process such as screen printing process, inkjet technology, coating technology etc, or any kind of thin film process such as lift-off process in micro-structuring technology. For example, the line width between the first catalyst electrode 110 and the second catalyst electrode 120 can be reduced to 0.03 mm scale if the line width is fabricated by the automatic screen printing machine while the line width can be miniaturized to 7 μm-20 nm if it is fabricated by the lift-off process in micro-structuring technology. Because the first catalyst electrode 110 and the second catalyst electrode 120 are fabricated in a coplanar configuration, it is beneficial to reducing manufacturing cost, labor hours and processing difficulty.

Figure 4A:
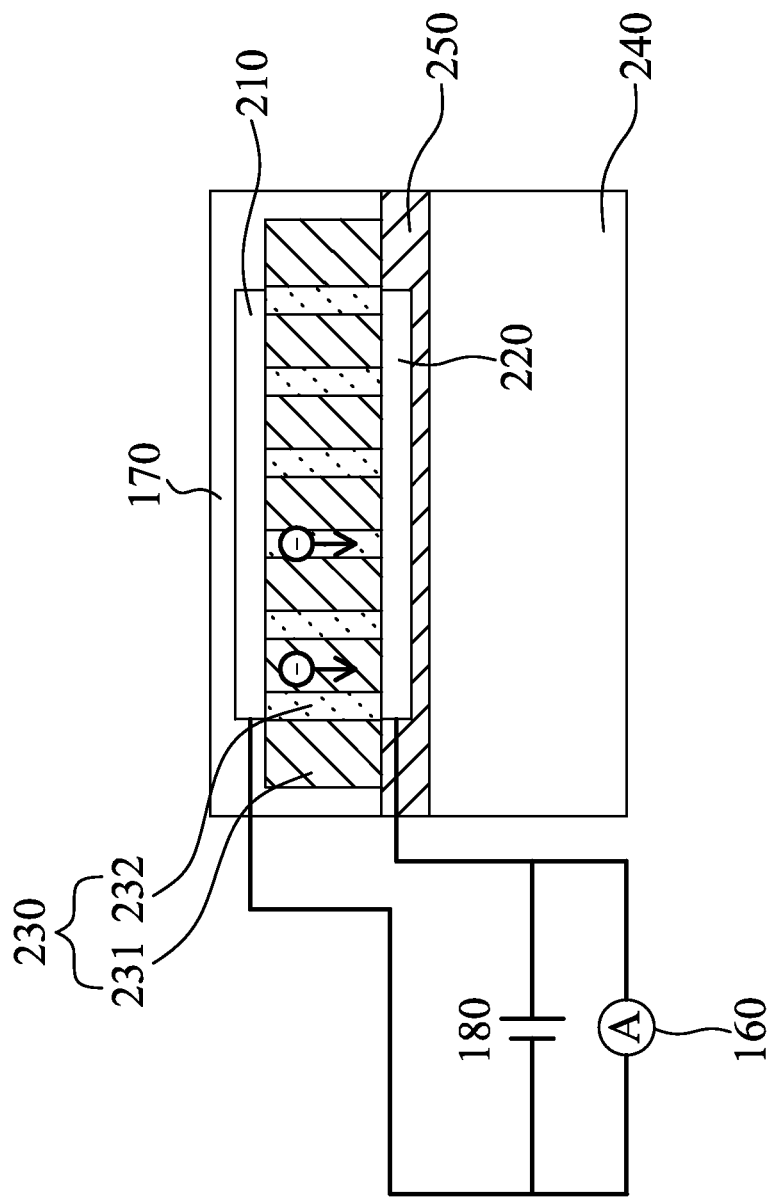
FIG. 4A is an illustrative schematic view for a current-type gas sensor in the second preferred exemplary embodiment of the present invention.

FIG. 4A is an illustrative schematic view for a current-type gas sensor in the second preferred exemplary embodiment of the present invention. In this preferred exemplary embodiment, contrasting to FIG. 2, the first catalyst electrode 210 is disposed on the layered structure 230 while the second catalyst electrode 220 is disposed under the layered structure 230. Moreover, the layered structure 230 is vertically laminated by multiple pairs of ionic conductive film 231 and high gas-permeability interlayer film 232. The orientation for all pairs of ionic conductive film 231 and high gas-permeability interlayer film 232 is almost perpendicular to boundaries formed by the layered structure 230 with the first catalyst electrode 210 and the second catalyst electrode 220 respectively. The high-k layer 250 is sandwiched between the layered structure 230 and conductivity promotion structure 240. The second catalyst electrode 220 is embedded in the high-k layer 250 with resultant manner that the second catalyst electrode 220 is enveloped by the high-k layer 250. Here, the high-k layer 250 has fixed content of lattice oxygen so it can be functioned as a referential gaseous layer. Besides, if the power supply 180 and the current detecting unit 160 in FIG. 4A are replaced by a voltage detecting unit (not shown), a voltage-type gas sensor is formed.

In this exemplary embodiment, the gap of the first catalyst electrode 210 and the second catalyst electrode 220 (namely the moving displacement of the free gas ions or free electrons) equals the thickness of the layered structure 230. The rest components with features and functions thereof in this exemplary embodiment are the same as those in the exemplary embodiment shown in FIG. 2, which are unnecessary to disclose here in redundant manner.

Figure 4B:
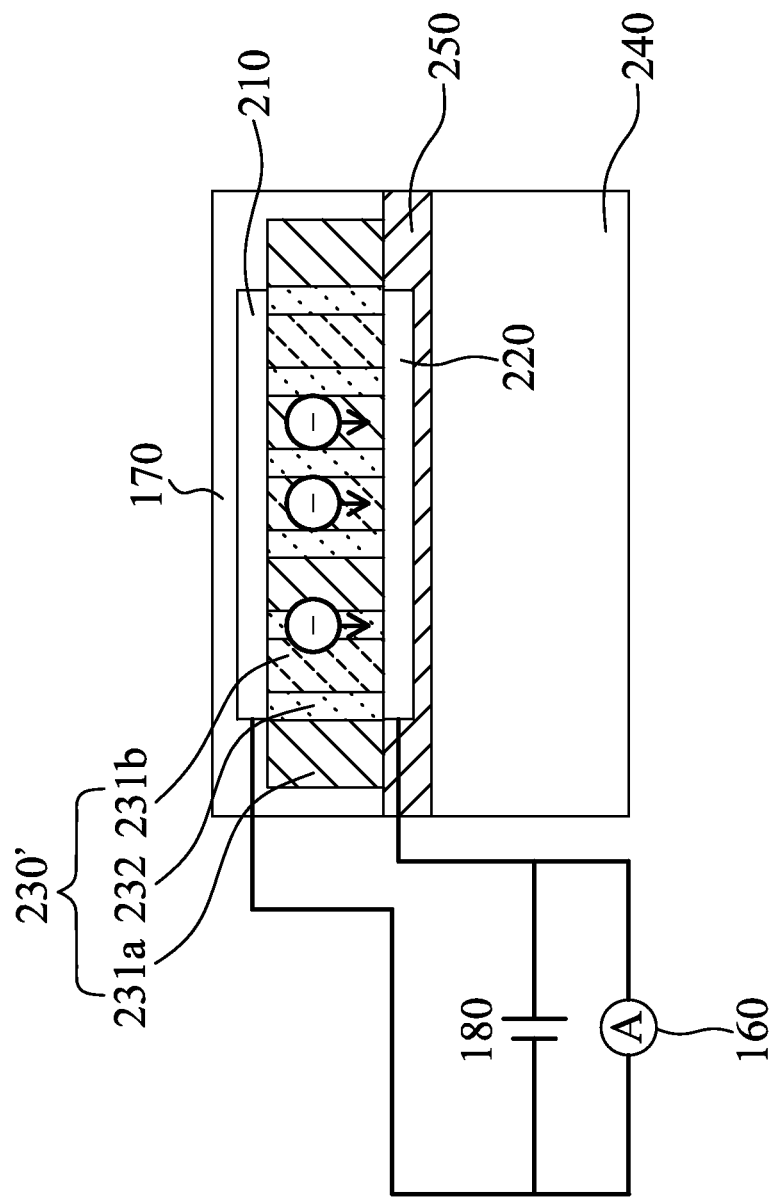
FIG. 4B is an illustrative schematic view for a current-type gas sensor in the third preferred exemplary embodiment of the present invention.

FIG. 4B is an illustrative schematic view for a current-type gas sensor in the third preferred exemplary embodiment of the present invention. In this preferred exemplary embodiment, contrasting to the layered structure 230 having a plurality of ionic conductive film 231 made by the same material in FIG. 4A, the corresponding layered structure 230' here is vertically laminated by multiple pairs of ionic conductive film 231a, 231b in respective different material and high gas-permeability interlayer film 232 in same material. Although the ionic conductive films 231a and 231b are formed in different material respectively in the third preferred exemplary embodiment, it is not limited to this status. In one embodiment, the multiple high gas-permeability interlayer films 232 can be also formed into respective different material.

Figure 4C:
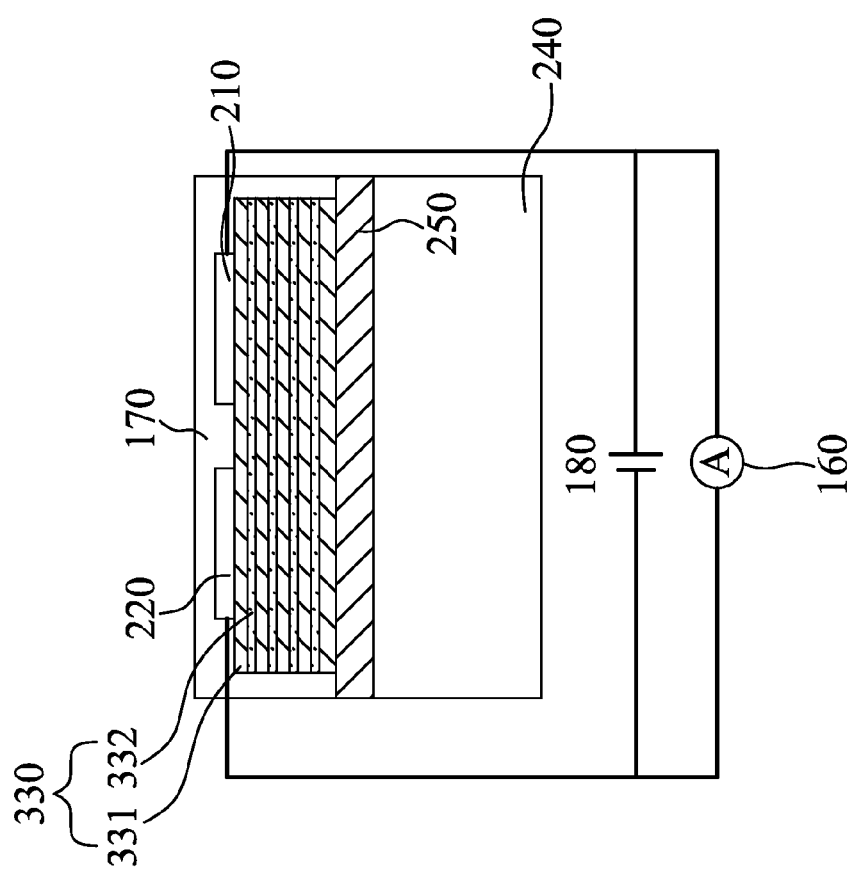
FIG. 4C is an illustrative schematic view for a current-type gas sensor in the fourth preferred exemplary embodiment of the present invention.

FIG. 4C is an illustrative schematic view for a current-type gas sensor in the fourth preferred exemplary embodiment of the present invention. In this preferred exemplary embodiment, contrasting to FIG. 2, the layered structure 330 is horizontally laminated by multiple pairs of ionic conductive film 331 and high gas-permeability interlayer film 332. The first catalyst electrode 210 and the second catalyst electrode 220 are disposed on the upper surface of the layered structure 330. The orientation for all pairs of ionic conductive film 331 and high gas-permeability interlayer film 332 is almost parallel to the first catalyst electrode 210 and second catalyst electrode 220. The rest components with features and functions thereof in this exemplary embodiment are the same as those in the exemplary embodiment shown in FIG. 2, which are unnecessary to disclose here in redundant manner.

Figure 4D:
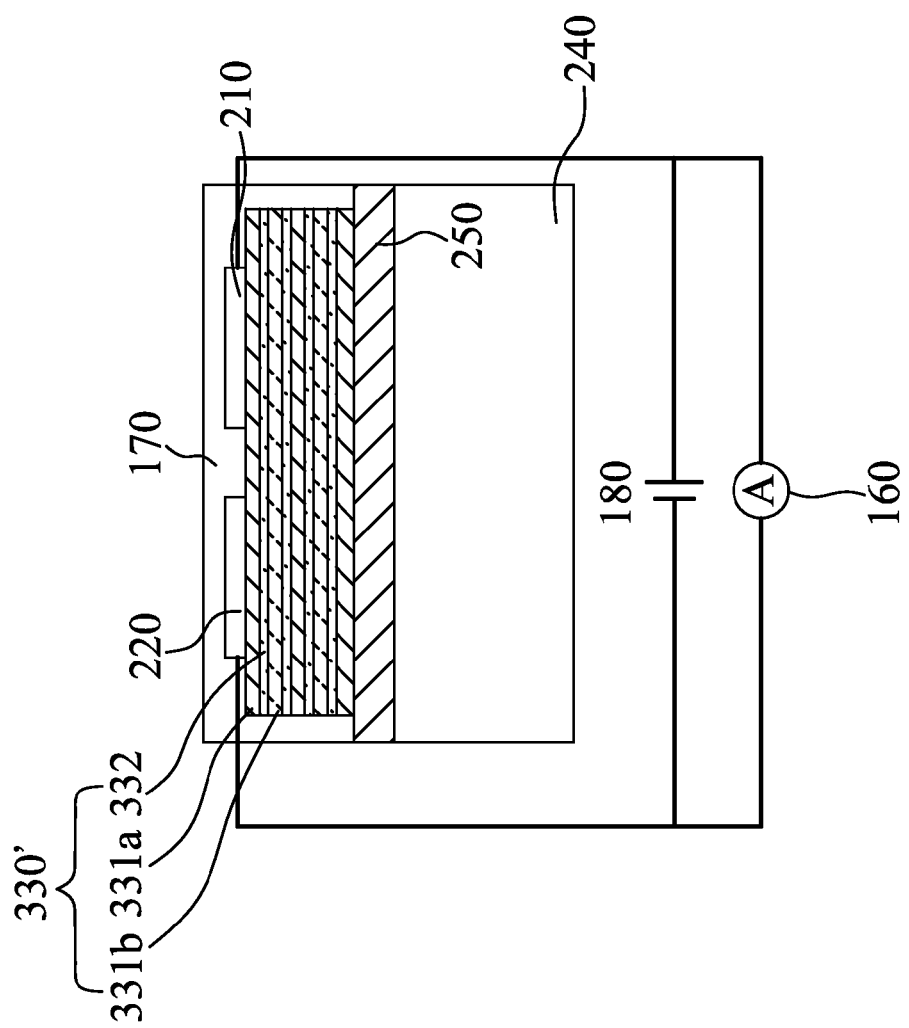
FIG. 4D is an illustrative schematic view for a current-type gas sensor in the fifth preferred exemplary embodiment of the present invention.

FIG. 4D is an illustrative schematic view for a current-type gas sensor in the fifth preferred exemplary embodiment of the present invention. In this preferred exemplary embodiment, contrasting to the plurality of ionic conductive films 331 being made by same material in FIG. 4C, the corresponding layered structure 330' here is horizontally laminated by multiple pairs of ionic conductive film 331a, 331b in respective different material.

Figure 5:
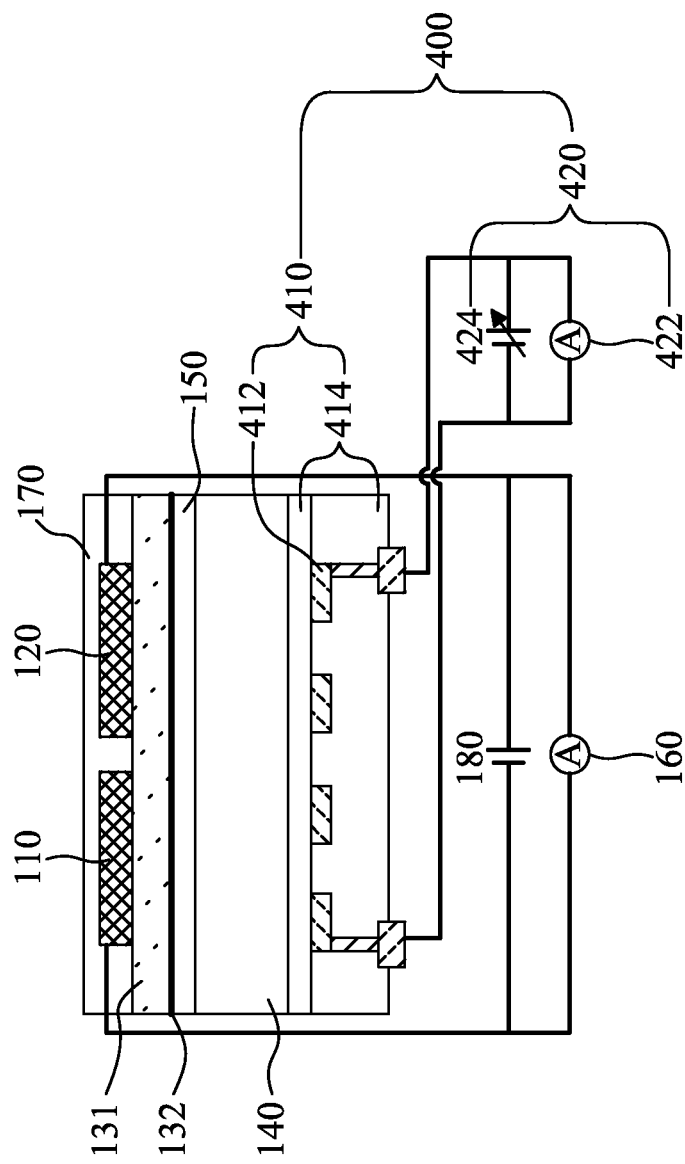
FIG. 5 is an illustrative schematic view for a current-type gas sensor in the sixth preferred exemplary embodiment of the present invention.

FIG. 5 is an illustrative schematic view for a current-type gas sensor in the sixth preferred exemplary embodiment of the present invention. In this preferred exemplary embodiment, contrasting to the gas sensor 100 in FIG. 2, the corresponding gas sensor here is additionally provided an active thermal control module 400. The active thermal control module 400 comprises a heating unit 410 and a temperature control unit 420. The heating unit 410 is used to heat the layered structure 130 while the temperature control unit 420 is used to monitor and control the heating unit 410 so the working temperature for the ionic conductive film 131 of the layered structure 130 can be constantly kept in a preset range.

Moreover, the heating unit 410 includes a heating filament 412 sheathed in an insulating coat layer 414 such that the overall heating unit 410 is closely attached beneath the bottom surface of the conductivity promotion structure 140. The material of the heating filament 412 is selected from metal with excellent electric properties such as nickel, gold, silver, platinum etc, while the material of the insulating coat layer 414 is selected insulating material such as alumina, zirconia, cerium oxide, magnesia, strontium titanate, barium titanate, lanthanum aluminate, lithium niobate etc. Besides, the disposing location of the heating filament 412 is not limited in the foregoing status as long as it can effectively heat the layered structure 130 without harmful side-effect. Accordingly, the heating filament 412 can be not only disposed in any location of non-sensing surface of the gas sensor but also disposed in the internal location of the gas sensor. The non-sensing surface of the gas sensor means that surface of the gas sensor excluding the sensing surface formed by the first catalyst electrode 110 and the second catalyst electrode 120.

The temperature control unit 420 further includes a current meter 422 and a logic circuit 424. The current meter 422 serves to detecting the heating current flowing through the heating filament 412. The logic circuit 424 is used to control the power output of the heating filament 412 according to the heating current therein. In physics, the resistance of the heating filament 412 is a function of the heating temperature, which means that the heating current of the heating filament 412 changes with heating temperature even external applied voltage is kept in constant. Accordingly, via measuring the fluctuation of the heating current by the current meter 422, the actual heating temperature of the heating filament 412 can be computed so the logic circuit 424 can precisely the power output of the heating filament 412 other than intelligently provides adequate voltage to the heating filament 412 for heating requirement to further constantly maintain the suitable working temperature for the gas sensor 100.

Figure 6:
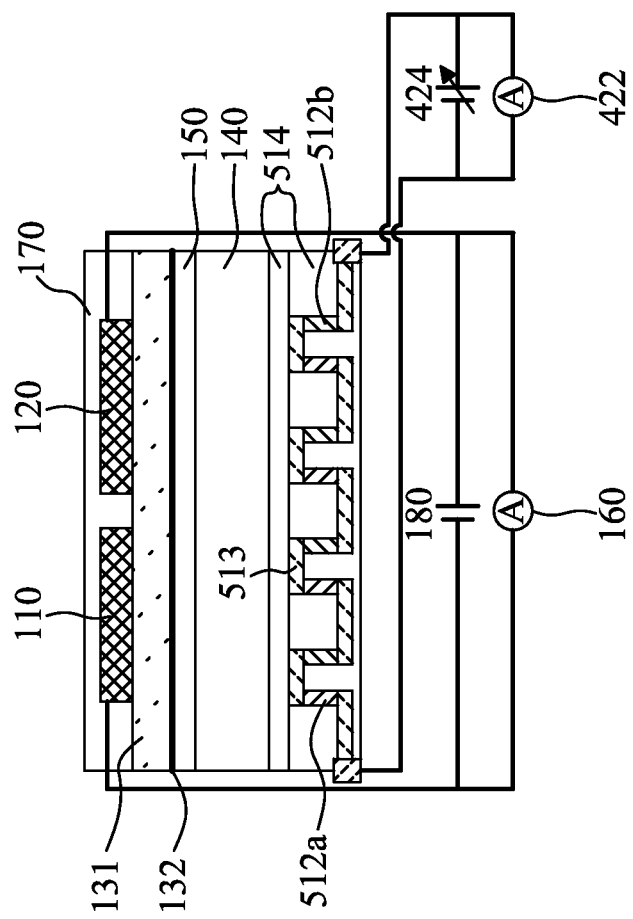
FIG. 6 is an illustrative schematic view for a current-type gas sensor equipped with an active thermal control module in the seventh preferred exemplary embodiment of the present invention.

FIG. 6 is an illustrative schematic view for a current-type gas sensor equipped with an active thermal control module in the seventh preferred exemplary embodiment of the present invention. In this preferred exemplary embodiment, contrasting to the additional heating filament 412 for the gas sensor in FIG. 5, the corresponding gas sensor here is additionally provided a conducting lamina 513 connecting to an electric couple including a N-type semiconductor texture 512a and a P-type semiconductor texture 512b. The conducting lamina 513, which is embedded in an insulating coat layer 514, is disposed under the bottom surface of the conductivity promotion structure 140. Via changing the flowing direction of the electric current passing the electric couple of N-type semiconductor texture 512a and P-type semiconductor texture 512b, the heating or cooling purposes of the gas sensor can be achieved by regulating the conducting lamina 513 into heating mode or cooling mode. The material of the N-type semiconductor texture 512a and P-type semiconductor texture 512b can selects from bismuth telluride, telluride selenide or tellurium, bismuth selenide etc., or any kind of combination from foregoing bismuth telluride, telluride selenide or tellurium, bismuth selenide etc.

As mentioned above, by taking advantage of semiconductor feature, an electric couple including the N-type semiconductor texture 512a and P-type semiconductor texture 512b is created, which is not the only possibility for the present invention. There are some more possibilities to create useful parts or components for the present invention by taking advantage of semiconductor feature. For example, anyone of foregoing bismuth telluride, telluride selenide or tellurium, bismuth selenide etc. in making the N-type semiconductor texture 512a (or P-type semiconductor texture 512b) can be selected to fabricate the conductivity promotion structure 140, 240 such that an additional P-type semiconductor texture 512b is fabricated on the non-sensing surface of the conductivity promotion structure 140, 240 via thick-film process/thin-film process or micro-electro-mechanical systems (MEMS). By this way, one semiconductor texture in the electric couple is directly replaced by the conductivity promotion structure 140, 240 to simplify fabricating process and to reduce manufacturing cost.

In a preferred exemplary embodiment, the constructing material for the ionic conductive film 131 can select from base material of zirconia, cerium oxide and bismuth oxide, which are doped by bi-valence and tri-valence cations in single/common mode, or can select from material of lanthanum molybdate ($LaMo_2O_9$) and perovskite (($La_{1-x}Sr_x$)($Ga_{1-y}Mg_y$)$O_{3-\delta}$). The high gas-permeability interlayer film 132 of the present invention can be formed via directly employing interface reaction of cladding material between two different materials. For example, the high gas-permeability interlayer film 132, 232 in FIGS. 2, 4C and 4D of the present invention can be fabricated by firstly constructing a substrate by insulating material containing low-valence ions such as magnesia, strontium titanate, lanthanum aluminate, barium titanate and lithium niobate etc, then plating the ionic conductive film 131 by tetra-valence material of zirconia or cerium oxide etc. Moreover, the vertical orientated ionic conductive film 231, 231a, 231b in FIGS. 4A and 4B of the present invention can be fabricated by directly employing sputtering process while the high gas-permeability interlayer film 232, 332 can be interposed into transition boundaries among columnar crystal structures, which are formed by the target material of alumina and zirconia.

Following factors should be considered in the material selections for the foregoing ionic conductive film 131, 231 and high gas-permeability interlayer film 132, 232. First factor group includes the matching status between the ionic conductive film 131, 231 and the high gas-permeability interlayer film 132, 232 such as thermal expansion coefficient, matching property of lattice and interface stress created in the process etc. Second factor group includes the chemical element difference and element valence difference in respective layers to prevent generating a chemical compound with bad gas permeability. Third factor group includes anti-reducing ability in respective layers. In considering this factor, a multi-layer design is adopted to enhance overall anti-reducing ability.

Besides, the constructing materials of the conductivity promotion structure 140, 240 can be categorized into insulation material, metallic alloy and semiconductor material. The insulation material includes magnesia, strontium titanate, lanthanum aluminate, lithium niobate etc. The metallic alloy includes stainless steel 17-4PH. The semiconductor material includes composite material of boron silicon and borosilicate group.

The foregoing description of the preferred embodiment of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to best explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like is not necessary limited the claim scope to a specific embodiment, and the reference to particularly preferred exemplary embodiments of the invention does not imply a limitation on the invention, and no such limitation is to be inferred. The invention is limited only by the spirit and scope of the appended claims. The abstract of the disclosure is provided to comply with the rules requiring an abstract, which will allow a searcher to quickly ascertain the subject matter of the technical disclosure of any patent issued from this disclosure. It is submitted with the understanding that it will not be used to interpret or limit the scope or meaning of the claims. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. A gas sensor, comprising:
    a layered structure comprising at least one ionic conductive film and at least one high gas-permeability interlayer film stacked in an alternative manner, wherein the thickness of the ionic conductive film is greater than or equivalent to that of the high gas-permeability interlayer film, the ionic conductive film is made of ionic material with its thickness in the range of 1 to 500 nanometers, and the ionic conductivity of the ionic conductive film is in the range of 0.02 to 1,000 S/cm;
    a first catalyst electrode and a second catalyst electrode disposed on the layered structure or at a lateral side of the layered structure with a gap therebetween, wherein a gas is ionized at the first catalyst electrode into gaseous ions, and the gaseous ions move to the second catalyst electrode via the high gas-permeability interlayer film of the layered structure such that the gaseous ions can be reduced by an reduction reaction at the second catalyst electrode;
    a conductivity promotion structure made of a material with electronic conductivity in the range of $10^{-5}$ to $10^5$ S/cm to provide free electrons to enhance the reduction reaction;

a high dielectric constant layer sandwiched between the layered structure and the conductivity promotion structure; and a detecting unit electrically connected to the first catalyst electrode and the second catalyst electrode.

2. The gas sensor of claim 1, further comprising an active thermal control module having a heating unit and a temperature control unit, wherein the heating unit is used to heat the layered structure, and the temperature control unit is used to monitor the heating unit and control the power output of the heating unit.

3. The gas sensor of claim 2, wherein the heating unit comprises a heating filament sheathed in an insulating coat layer, and the heating unit is attached to the conductivity promotion structure, and the temperature control unit controls the power output of the heating filament via detecting a heating current flowing through the heating filament.

4. The gas sensor of claim 3, wherein the heating unit comprises an electric couple embedded in an insulating coat layer, the temperature control unit controls the power output of the heating unit via changing the flowing direction of the electric current passing the electric couple.

5. The gas sensor of claim 1, wherein the orientation of the ionic conductive film and the high gas-permeability interlayer film are perpendicular or parallel to at least one of the first catalyst electrode and the second catalyst electrode.

6. The gas sensor of claim 5, wherein the first catalyst electrode and the second catalyst electrode are respectively disposed at two opposite sides of the layered structure, and the second catalyst electrode is sandwiched between the layered structure and the high dielectric constant layer.

7. The gas sensor of claim 5, wherein the high gas-permeability interlayer film is interposed between the ionic conductive film and the high dielectric constant layer.

8. The gas sensor of claim 1, wherein the layered structure comprises two ionic conductive films adjacent to each other, each of the ionic conductive films is respectively made of individual different material.

9. The gas sensor of claim 8, wherein the high gas-permeability interlayer film is interposed between the ionic conductive films.

10. The gas sensor of claim 1, further comprising a gas diffusion layer covering at least the layered structure and the first catalyst electrode.

11. The gas sensor of claim 1, wherein the free electrons provided by the conductivity promotion structure penetrate through the high dielectric constant layer to reach the layered structure or the second catalyst electrode by tunneling effect.

* * * * *